United States Patent
Winterbottom et al.

(10) Patent No.: US 7,291,345 B2
(45) Date of Patent: **\*Nov. 6, 2007**

(54) FORMABLE AND SETTABLE POLYMER BONE COMPOSITE AND METHOD OF PRODUCTION THEREOF

(75) Inventors: John Winterbottom, Jackson, NJ (US); David Kaes, Toms River, NJ (US)

(73) Assignee: Osteotech, Inc., Eatontown, NJ (US)

( * ) Notice: Subject to any disclaimer, the term of this patent is extended or adjusted under 35 U.S.C. 154(b) by 150 days.

This patent is subject to a terminal disclaimer.

(21) Appl. No.: 10/735,135

(22) Filed: Dec. 12, 2003

(65) Prior Publication Data
US 2005/0008672 A1  Jan. 13, 2005

Related U.S. Application Data

(60) Provisional application No. 60/432,968, filed on Dec. 12, 2002.

(51) Int. Cl.
C12N 5/00 (2006.01)
C12N 5/02 (2006.01)
C12N 5/08 (2006.01)

(52) U.S. Cl. ............ 424/400; 424/422; 424/93.1; 424/600

(58) Field of Classification Search ........ 424/400, 424/422, 423, 93.1, 600; 435/325, 372, 395
See application file for complete search history.

(56) References Cited

U.S. PATENT DOCUMENTS

| | | | |
|---|---|---|---|
| 3,892,649 A | 7/1975 | Phillips et al. | 204/181 |
| 3,919,773 A | 11/1975 | Freeman | 32/10 A |
| 3,949,073 A | 4/1976 | Daniels et al. | 424/177 |
| 4,183,874 A | 1/1980 | Fan et al. | 525/100 |
| 4,551,156 A | 11/1985 | Li | 55/16 |
| 4,645,503 A | 2/1987 | Lin et al. | 623/16 |
| 4,783,504 A | 11/1988 | St. Clair et al. | 525/72 |
| 5,162,445 A | 11/1992 | Powers et al. | 525/333.4 |
| 5,246,782 A | 9/1993 | Kennedy et al. | 428/421 |
| 5,262,461 A | 11/1993 | Serizawa et al. | 524/262 |
| 5,324,519 A | 6/1994 | Dunn et al. | 424/426 |
| 5,333,626 A | 8/1994 | Morse et al. | 128/898 |
| 5,468,544 A | 11/1995 | Marcolongo et al. | 428/224 |
| 5,513,662 A | 5/1996 | Morse et al. | 128/898 |
| 5,552,454 A | 9/1996 | Kretschmann et al. | |
| 5,606,000 A | 2/1997 | Jadhav et al. | 528/29 |
| 5,624,463 A | 4/1997 | Stone et al. | |
| 5,626,861 A | 5/1997 | Laurencin et al. | 424/426 |
| 5,736,372 A | 4/1998 | Vacanti et al. | 435/180 |
| 5,766,618 A | 6/1998 | Laurencin et al. | 424/426 |
| 5,837,752 A | 11/1998 | Shastri et al. | |
| 5,846,484 A | 12/1998 | Scarborough et al. | 422/28 |
| 5,948,386 A | 9/1999 | Katti et al. | 424/1.77 |
| 6,027,744 A | 2/2000 | Vacanti et al. | 424/426 |
| 6,132,468 A | 10/2000 | Mansmann | 623/20.16 |
| 6,165,486 A | 12/2000 | Marra et al. | 424/423 |
| 6,183,498 B1 | 2/2001 | Devore et al. | |
| 6,294,187 B1 | 9/2001 | Boyce et al. | |
| 6,352,667 B1 | 3/2002 | English | 264/328.17 |
| 6,376,573 B1 | 4/2002 | White et al. | |
| 6,399,693 B1 | 6/2002 | Brennan et al. | 524/494 |
| 6,406,498 B1 | 6/2002 | Törmälä et al. | 623/23.75 |
| 6,432,436 B1 | 8/2002 | Gertzman et al. | 424/423 |
| 6,441,073 B1 | 8/2002 | Tanaka et al. | |
| 6,696,073 B2 | 2/2004 | Boyce et al. | |
| 6,933,328 B2 | 8/2005 | Schacht | |
| 2002/0035401 A1* | 3/2002 | Boyce et al. | 623/23.51 |
| 2002/0098222 A1 | 7/2002 | Wironen et al. | 424/423 |
| 2003/0039676 A1 | 2/2003 | Boyce et al. | |
| 2003/0045942 A1 | 3/2003 | Lai et al. | |
| 2003/0114552 A1 | 6/2003 | Schacht | |
| 2003/0180344 A1 | 9/2003 | Wise et al. | |
| 2003/0236573 A1 | 12/2003 | Evans et al. | |
| 2004/0024457 A1 | 2/2004 | Boyce et al. | |
| 2004/0034434 A1 | 2/2004 | Evans et al. | |
| 2004/0064193 A1 | 4/2004 | Evans et al. | |
| 2004/0138758 A1 | 7/2004 | Evans et al. | |
| 2004/0146543 A1 | 7/2004 | Shimp et al. | |
| 2005/0008620 A1 | 1/2005 | Shimp et al. | |
| 2005/0129726 A1 | 6/2005 | Liebschner | |
| 2005/0238683 A1 | 10/2005 | Adhikari et al. | |
| 2005/0281856 A1 | 12/2005 | McGlohorn et al. | |

FOREIGN PATENT DOCUMENTS

WO    WO 98/19718    5/1998

OTHER PUBLICATIONS

U.S. Appl. No. 10/639,912, filed Aug. 12, 2003, Shimp et al.
U.S. Appl. No. 10/681,651, filed Oct. 8, 2003, Shimp et al.
International Search Report for PCT/US03/25417.
International Search Report for PCT/US03/39704.
Baker, Gregory L., http://www.cem.msu.edu/~gradoff/brochf/Baker.htm, printed Aug. 2002.
Boesch, P., "Bone Grafting with Fibrin Glue", *Wiener Klinische Worchenschroft Supplementum*, 93, No. 124, pp. 3-26, 1981.
Han, et al., "Synergistic Effects of Lecithin and Human DBM on Bone Induction in Nude Rats", *Society for Biomaterials*, 28th Annual Meeting Transactions, 2002 (abstract).
Hooper, et al., "Diphenolic Monomers Derived from the Natural Amino Acid α-L-Tyrosine: An Evaluation of Peptide Coupling Techniques", *Journal of Bioactive and Compatible Polymers* 10, 327-340 (1995).

(Continued)

*Primary Examiner*—Ruth A. Davis
(74) *Attorney, Agent, or Firm*—C. Hunter Baker; Choate, Hall & Stewart LLP

(57) ABSTRACT

A composite osteoimplant. The osteoimplant includes a polymer and bone-derived particles. The composite is adapted and constructed to be formable during or immediately prior to implantation and to be set after final surgical placement.

34 Claims, No Drawings

OTHER PUBLICATIONS

Nazhat, S.N., et al., "Dynamic Mechanical Behaviour of Modified Hydroxyapatite Reinforced Polyethylene Composites", *Fifth World Biomaterials Congress*, p. 83, May 29-Jun. 2, 1996.

Satish Pulapura, et al., "Tyrosine-Derived Polycarbonates: Backbone-Modified "Pseudo" -Poly (Amino Acids) Designed for Biomedical Applications", *Biopolymers* 32, 411-417 (1992).

"Silane Coupling Agent", http://www.apr.co.kr/silaneen.htm, printed Aug. 7, 2002.

Simmons, D.M., et al., "Evaluation of collagen cross-linking techniques for the stabilization of tissue matrices", *Biotechnol. Appl. Biochem.* 17, 23-29 (1993) (abstract only).

Tangpasuthadol, Varawut, "Thermo-Mechanical Properties and Hydrolytic Degradation of Tyrosine-Derived Polymers for Use in Biomedical Applications", Ph.D. Dissertation, Rutgers, The State University of New Jersey, (Jan. 1999).

Whittaker, et al., "Matrix Metalloproteinases and their Inhibitors—Current Status and Future Challenges", *Celltransmissions*, 17, prior to Jun. 13, 2002.

Zhiyuan Zhong, et al., "Calcium methoxide initiated ring-opening polymerization of $\epsilon$-caprolactone and L-lactide", *Polymer Bulletin* 46, 51-57 (2001).

Schmitz, et al., "A Preliminary Study of the Osteogenic Potential of a Biodegradable Alloplastic-Osteoinductive Alloimplant", *Clinical Orthopaedics and Related Research*, 237:245-255 (1988).

* cited by examiner

FORMABLE AND SETTABLE POLYMER BONE COMPOSITE AND METHOD OF PRODUCTION THEREOF

This application claims the priority of U.S. Provisional Application No. 60/432,968, filed Dec. 12, 2002.

FIELD OF THE INVENTION

This invention pertains to a polymer-bone composite, and more particularly, to a composite that can be formed in situ or immediately prior to implantation.

BACKGROUND OF THE INVENTION

Bone is a composite material composed of impure hydroxyapatite, collagen, and a variety of noncollagenous proteins, as well as embedded and adherent cells. Bone can be processed into an implantable material, such as an allograft, for example, by treating it to remove the cells, leaving behind the extracellular matrix. The processed bone biomaterial can have a variety of properties, depending upon the specific processes and treatments applied to it, and may be combined with other biomaterials to form a composite that incorporates characteristics of both bone and the other biomaterials. For example, bone-derived materials may be processed into load-bearing mineralized grafts that support and integrate with the patient's bone or may alternatively be processed into soft, moldable or flowable demineralized bone biomaterials that have the ability to induce a cellular healing response.

The use of bone grafts and bone substitute materials in orthopedic medicine is well known. While bone wounds can regenerate without the formation of scar tissue, fractures and other orthopedic injuries take a substantial time to heal, during which the bone is unable to support physiologic loads. Metal pins, screws, and meshes are frequently required to replace the mechanical functions of injured bone. However, metal is significantly stiffer than bone. Use of metal implants may result in decreased bone density around the implant site due to stress shielding. Furthermore, some metal implants are permanent and unable to participate in physiological remodeling.

Bone's cellular healing processes, using bone tissue formation by ostoblast cells coordinated with bone and graft resorption by osteoclast cells, permit bone grafts and certain bone substitute materials to remodel into endogenous bone that is almost indistinguishable from the original. However, the use of bone grafts is limited by the available shape and size of grafts and the desire to optimize both mechanical strength and degradation rate. Variations in bone size and shape among patients (and donors) also make bone grafts a less optimal substitute material. Bone substitute materials and bone chips are quickly remodeled but cannot immediately provide mechanical support. In contrast, cortical bone grafts can support physiological stresses but remodel slowly.

Thus, it is desirable to have a bone substitute material for structural grafts that may be produced in larger quantities than grafts derived solely from bone and that may be fabricated into shapes without being limited by the shape of the originating tissue.

Additionally, it is desirable to have a bone substitute material that may be adapted to a desired shape during implantation.

SUMMARY OF THE INVENTION

The invention combines the advantages of a formable and a solid implant. The composite can bear weight and other mechanical loads immediately after setting in its rigid state. During implantation, the composite is able to infiltrate and mechanically interlock with porous structures disposed about the implant site. The formable composite can be molded or formed to conform to adjacent anatomical and surgical structures (e.g., other struts, plates, and implants used during surgery) but remains anchored at the implant site in its rigid state, without unwanted deformation or motion. After the composite is implanted and hardened, it may be machined to further conform the surface of the implant to the surface of the surrounding tissue or to facilitate insertion of additional implants or devices. In addition, the composite may be irrigated with saline, water, or other appropriate liquids before, during, or after implantation without displacing, changing the shape of, or otherwise adversely modifying the final implant.

In one aspect, the invention is a composite osteoimplant including a polymer and bone-derived particles. The composite is adapted and constructed to be formable during or immediately prior to implantation and to be set under predetermined conditions. The composite may be formable at room temperature. Alternatively, the composite may become formable when heated to a temperature greater than about 40° C. but not be as formable at about 37° C. For example, the composite may become formable when heated to a temperature greater than about 45° C., 50° C., 55° C., 60° C., 70° C., 80° C., or 90° C. The composite may become more set by increasing the cross-link density of the polymer component. The composite may further include a monomer and become set when the monomer is covalently incorporated into the polymer.

The composite may further include one or more of bone marrow, a biomolecule, a small molecule, a bioactive agent, calcium phosphate, calcium carbonate, and cells. For example, the composite may include one or more of a nucleic acid vector, mesenchymal stem cells, osteoblasts, osteoclasts, and fibroblasts. The nucleic acid vector, when introduced into a cell, may increase the cell's production of bone morphogenetic proteins. The osteoimplant may be adapted and constructed to be irrigated following implantation without substantially changing its shape. The bone-derived particles may be about 10% to about 99% by weight of the composite, for example, about 25% to about 50%.

A surface of the bone-derived particles may be modified with one or more of a biomolecule, a small molecule, a bioactive agent, and a non-biologically active material. Collagen fibers at the surface of the bone-derived particles may be exposed and may optionally be partially or fully separated from one another. The exposed collagen fibers may be derivatized with one or more of a biomolecule, a small molecule, a bioactive agent, and a non-biologically active material. The polymer may be biodegradable or non-biodegradable and may be a mixture or co-polymer of biodegradable polymers, non-biodegradable polymers, or both.

The osteoimplant may include a plurality of pieces of composite that are joined together, for example, with one or more of an adhesive, a mechanical fastener, and ultrasonic bonding. The composite may be adapted and constructed to be formed in a mold.

The distribution of bone particles within the composite may vary within the composite with respect to one or more of volume fraction, size, density, size distribution, and shape. At least a portion of the bone-derived particles in the composite may be elongate, and the arrangement of particles within the composite may be isotropic or anisotropic. The relative alignment of elongate bone-derived particles in the composite may be different in a first portion, a second portion, and/or subsequent portions of the composite. The bone-derived particles and the polymer may be linked with a silane coupling agent. In another aspect, the invention is a method of preparing an osteoimplant. The method includes the steps of forming a composite comprising bone-derived particles and a polymer into a predetermined shape and causing the polymer to set. The method may further include combining the composite with autogenous tissue, including autograft bone.

The predetermined shape may be that of a wound site in a bone and the step of forming may include packing the wound site with the composite. Before the composite is formed into a shape, it may be heated to a temperature at which it is formable, and the polymer may be set by allowing it to cool to ambient temperature or body temperature. Alternatively, the polymer may be set by increasing the cross-link density of the polymer. The osteoimplant may further include a mechanical fastener, and the composite may be formed so as to retain the mechanical fastener after the polymer is set.

In another embodiment, the invention is a kit for producing an osteoimplant. The kit includes a polymer adapted and constructed to be formable under predetermined conditions and set after final surgical placement of the osteoimplant and bone-derived particles. Under the predetermined conditions, the polymer and the bone-derived particles may be combined and formed into a predetermined shape. The predetermined conditions may include a temperature greater than about 40° C. The polymer may be set by exposing it to an energy source for a predetermined period of time. The osteoimplant may be adapted and constructed to be irrigated following implantation without substantially changing its shape. The predetermined shape may be defined by a mold. The composite may be adapted and constructed to be implanted by forming it within a tissue site.

In another aspect, the invention is a method of producing a composite for use in an osteoimplant. The method comprises providing a polymer adapted and constructed to be formable under a first predetermined condition and set under a second predetermined condition, providing a plurality of bone-derived particles, and combining the polymer and the plurality of bone-derived particles under the first predetermined condition. The polymer and the plurality of bone-derived particles may further be combined with autogenous tissue. Before the step of combining, the polymer may be heated to a temperature at which it is formable. After combining, the composite may be allowed to cool to ambient or body temperature. A mechanical fastener may be incorporated into the composite.

The method may further include forming a second composite and causing it to set, following which the two composites are joined together to form an osteoimplant. The method may further include machining the composite into a shape before or after the step of forming, or any combination of these.

The method may further include combining bone-derived particles and a polymer to produce the composite. The particles and the polymer may be combined by pressing a mixture of polymer and bone-derived particles, hand mixing bone-derived particles into formable polymer, heating the polymer, solvent casting a polymer and bone-derived particles, injection molding, extrusion forming, pressing a coating of bone-derived particles into a sheet of polymer, and combining the polymer with a solvent. The composite may be formed by making a shape from the composite in a mold or arranging the composite in a tissue site.

The composite may be adapted to be formable into a shape of a wound site in a bone or to be shaped in a mold. The method may further comprise producing a second composite and joining the composites together to form an osteoimplant, for example, with one or more of an adhesive, a mechanical fastener, and ultrasonic bonding.

The composite may be adapted and constructed to be formed into a shape in a mold or a tissue site under the predetermined conditions. The composite may become set because the cross-link density of the polymer is increased. A monomer may be combined with the plurality of bone particles and the polymer, and the composite may become set when the monomer is incorporated into the polymer. The composite may become set when the polymer is brought to a temperature less than a temperature at which the polymer is formable.

Definitions

"Anisotropic": The term "anisotropic," as used herein, describes a characteristic of a material that varies with the axis of measurement.

"Biomolecules": The term "biomolecules," as used herein, refers to classes of molecules (e.g., proteins, amino acids, peptides, polynucleotides, nucleotides, carbohydrates, sugars, lipids, nucleoproteins, glycoproteins, lipoproteins, steroids, etc.) that are commonly found in cells and tissues, whether the molecules themselves are naturally-occurring or artificially created (e.g., by synthetic or recombinant methods). For example, biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible," as used herein is intended to describe materials that, upon administration in vivo, do not induce undesirable long term effects.

"Biodegradable": As used herein, "biodegradable" materials are materials that degrade under physiological conditions to form a product that can be metabolized or excreted without damage to organs. Biodegradable materials are not necessarily hydrolytically degradable and may require enzymatic action to fully degrade. Biodegradable materials also include materials that are broken down within cells.

"Composite": As used herein, the term "composite" is used to refer to a unified combination of two or more distinct materials.

"Formable": As used herein, "formable" materials are those that can be shaped by mechanical deformation. Exemplary methods of deformation include, without limitation, injection molding, extrusion, pressing, casting, rolling, and molding. In one embodiment, formable materials may be shaped by hand or using hand-held tools, much as an artist manipulates clay.

"Glass Transition Temperature": As used herein, the term "glass transition temperature" ($T_g$) indicates the lowest temperature at which an amorphous or partially amorphous polymer is considered softened and possibly flowable. As referred to herein, the value of $T_g$ is to be determined using differential calorimetry as per ASTM Standard E1356-98 "Standard Test Method for Assignment of the Glass Transition Temperatures by Differential Scanning Calorimetry or Differential Thermal Analysis."

"Isotropic": As used herein, the term "isotropic" is used to describe a characteristic of a material that does not vary with the axis of measurement.

"Melting Temperature": As used herein, the term "melting temperature" ($T_m$) is defined as the temperature, at atmospheric pressure, at which a polymer changes its state from solid to liquid. As referred to herein, the value of $T_m$ is the value of $T_{pm1}$ as determined according to per ASTM Standard D3418-99 "Standard Test Method for Transition Temperatures of Polymers By Differential Scanning Calorimetry."

"Osteoinductive": As used herein, the term "osteoinductive" is used to refer to the ability of a substance to recruit cells from the host that have the potential for forming new bone and repairing bone tissue. Most osteoinductive materials can stimulate the formation of ectopic bone in soft tissue.

"Osteoconductive": As used herein, the term "osteoconductive" is used to refer to the ability of a non-osteoinductive substance to serve as a suitable template or substrate along which bone may grow.

"Osteoimplant": As used herein, the term "osteoimplant" does not imply that the implant contains a specific percentage of bone or has a particular shape, size, configuration or application.

"Polynucleotide," "nucleic acid," or "oligonucleotide": The terms "polynucleotide," "nucleic acid," or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Polypeptide", "peptide", or "protein": According to the present invention, a "polypeptide," "peptide," or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polysaccharide", "carbohydrate" or "oligosaccharide": The terms "polysaccharide," "carbohydrate," or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Settable": As used herein, the term "settable" refers to a material that may be rendered more resistant to mechanical deformation with respect to a formable state.

"Set": As used herein, the term "set" refers to the state of a material that has been rendered more resistant to mechanical deformation with respect to a formable state.

"Small molecule": As used herein, the term "small molecule" is used to refer to molecules, whether naturally-occurring or artificially created (e.g., via chemical synthesis), that have a relatively low molecular weight. Typically, small molecules have a molecular weight of less than about 5000 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present invention.

"Bioactive agents": As used herein, the term "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, antihistamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents. In a certain preferred embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeial Convention, Inc., Rockville Md., 2001, each of which is incorporated herein by reference.

DETAILED DESCRIPTION OF CERTAIN PREFERRED EMBODIMENTS

The invention includes providing bone or other fill material and a biocompatible polymer to form a composite. The composite is adapted and constructed to be formable in a particular condition. For example, the composite may be formable after heating to or above a predetermined temperature. After forming, the composite is rendered less formable, for example, by cooling or cross-linking.

The composite may be molded by a surgeon or other skilled operator either immediately prior to implantation into a tissue site, during implantation into the site, and/or for a period after implantation into the site. Thus, the surgeon does not have to prepare an implant having the exact shape of the tissue site prior to surgery or prepare a site for a particular implant configuration. Instead, the implant may be shaped in situ.

Preparation of Bone

The bone particles employed in the preparation of the inventive bone particle-containing compositions can be obtained from cortical, cancellous and/or corticocancellous bone which may be of autogenous, allogenic, transgenic, and/or xenogeneic origin. Preferably, the bone particles are obtained from cortical bone of allogenic origin. Porcine and bovine bone are particularly advantageous types of xenogeneic bone tissue which can be used individually or in combination as sources for the bone particles. Particles are formed by milling whole bone to produce fibers, chipping whole bone, cutting whole bone, fracturing whole bone in liquid nitrogen, or otherwise disintegrating the bone tissue. Particles can optionally be sieved to produce particles in a specific size range.

In one embodiment, the bone particles have a size (i.e., the largest dimension) between about 50 μm and about 1 mm, for example, between about 100 μm and about 1 mm, to optimize ease of manipulation of the composite. Both smaller and larger particles may also be used in the composites of the invention. For example, bone particles with a largest dimension smaller than about 40 μm, about 30 μm, about 20 μm, or about 10 μm may be used. Larger particles, e.g., about 2-3 mm across or greater, may also be employed. The desired particle size and distribution will depend in part on the implant site, size, and shape. Large particles will reduce the possible resolution of a desired shape. For example, a composite with large particles may be difficult to form into a shape having small nooks or other details. The particle size will also affect the speed with which heat retained in the particles is released to the surrounding polymer (see below).

Alternatively or in combination, bone particles generally characterized as elongate and possessing relatively high median length to median thickness ratios can be utilized herein. Such elongate particles can be readily obtained by any one of several methods, e.g., by milling or shaving the surface of an entire bone or relatively large section of bone. Employing a milling technique, optionally followed by sorting and/or separating by length, diameter, or both, one can obtain elongate bone particles possessing a median length of from about 2 to about 200 mm or more, for example, from about 10 to about 100 mm, a median thickness of from about 0.05 to about 2 mm, for example, from about 0.2 to about 1 mm and a median width of from about 1 mm to about 20 mm, for example, from about 2 to about 5 mm. These elongate bone particles can possess a median length to median thickness ratio of at least about 50:1 up to about 500:1 or more, for example, from about 50:1 to about 100:1, and a median length to median width ratio from about 10:1 to about 200:1, for example, from about 50:1 to about 100:1. The milling process may be optimized to adjust the size of the bone particles and the size distribution. The mechanical strength, elastic modulus, and anisotropy of the implant can be tailored by adjusting the weight percent of the various shapes (elongate, particlulate, etc.) of bone particles utilized in the composite. Elongate and more evenly dimensioned particles may be used alone or in mixtures in any ratio between 0% and 100% elongate particles.

Another procedure for obtaining elongate bone particles, particularly useful for pieces of bone of up to about 100 mm in length, is the bone processing mill described in commonly assigned U.S. Pat. No. 5,607,269, the contents of which are incorporated herein by reference. Use of this bone mill results in the production of long, thin strips which quickly curl lengthwise to provide tubular-like bone particles. If desired, elongate bone particles can be graded into different sizes to reduce or eliminate any less desirable size(s) of particles which may be present. In overall appearance, elongate bone particles can be described as filaments, fibers, threads, slender or narrow strips, etc.

The bone particles are optionally demineralized in accordance with known and conventional procedures in order to reduce their inorganic mineral content. Demineralization methods remove the inorganic mineral component of bone by employing acid solutions. Such methods are well known in the art, see for example, Reddi et al., *Proc. Nat. Acad Sci* (1972) 69: 1601-1605, the contents of which are incorporated herein by reference. The strength of the acid solution, the shape of the bone particles and the duration of the demineralization treatment will determine the extent of demineralization. Reference in this regard may be made to Lewandrowski et al., *J Biomed Materials Res*, (1996) 31: 365-372, and U.S. Pat. No. 5,290,558, the contents of both of which are incorporated herein by reference.

In a preferred demineralization procedure, the bone particles are subjected to a defatting/disinfecting step which is followed by an acid demineralization step. A preferred defatting/disinfectant solution is an aqueous solution of ethanol. Ordinarily, at least about 10 to about 40 percent by weight of water (i.e., about 60 to about 90 weight percent of defatting agent such as alcohol) should be present in the defatting/disinfecting solution to remove lipids and disinfect the bone particles within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. The acid solution also disinfects the bone by killing microorganisms and viruses. Acids which can be employed in this step include inorganic acids such as hydrochloric acid and organic acids such as peracetic acid. After acid treatment, the demineralized bone particles are rinsed with sterile water to remove residual amounts of acid. Where elongate bone particles are employed, some entanglement of the demineralized bone particles will result. The demineralized bone particles can then be immediately shaped into any desired configuration or stored under aseptic conditions, advantageously in a lyophilized state, for processing at a later time. As an alternative to aseptic processing and storage, the particles can be shaped into a desired configuration and sterilized using suitable methods known to those skilled in the art.

As used herein, the phrase "superficially demineralized" as applied to the bone particles refers to bone particles possessing at least about 90 weight percent of their original inorganic mineral content. Superficial demineralization produces particles containing a mineralized core. The phrase "partially demineralized" as applied to the bone particles refers to bone particles possessing from about 8 to about 90 weight percent of their original inorganic mineral content, and the phrase "fully demineralized" as applied to the bone particles refers to bone particles possessing less than about 8, preferably less than about 1, weight percent of their original inorganic mineral content. The unmodified term "demineralized" as applied to the bone particles is intended to cover any one or combination of the foregoing types of demineralized bone particles.

Mixtures or combinations of one or more of the foregoing types of bone particles can be employed. For example, one or more of the foregoing types of demineralized bone particles can be employed in combination with nondemineralized bone particles, i.e., bone particles that have not been subjected to a demineralization process. Nondemineralized, non-elongate bone particles will also function much like ceramic inclusions, increasing the compressive strength of the composite. Nondemineralized bone, including nondemineralized portions of partially demineralized bone, is itself a fiber-reinforced composite, increasing the bending and tensile stress the composite can withstand before the bone particles fracture.

The bone particles in the composite also play a biological role. Non-demineralized bone particles bring about new bone ingrowth by osteoconduction. Demineralized bone particles likewise play a biological role in bringing about new bone ingrowth by osteoinduction. Both types of bone particles are gradually remodeled and replaced by new host bone as degradation of the composite progresses over time.

The differential in strength, osteogenicity and other properties between partially and fully demineralized bone particles on the one hand and non-demineralized and superficially demineralized bone particles on the other hand can be exploited. For example, nondemineralized and/or superficially demineralized bone particles can be concentrated in that region of the osteoimplant which will be directly subjected to loading during and/or after implantation. In order to increase the compressive strength of the osteoimplant, the ratio of nondemineralized and/or superficially demineralized bone particles to partially or fully demineralized bone particles may favor the former, and vice versa. Thus, the use of various types of bone particles can be used to control the overall mechanical and biological properties, i.e., the strength, osteoconductivity and/or osteoinductivity, etc., of the osteoimplant.

The amount of each individual type of bone particle employed can vary widely depending on the mechanical and biological properties desired. Thus, mixtures of bone particles of various shapes, sizes, and/or degrees of demineralization may be assembled based on the desired mechanical, thermal, and biological properties of the composite. In addition or alternatively, composites may be formed having a single type of one particle or with multiple sections, each having a different type or mixture of bone particles. Suitable amounts of particle types can be readily determined by those skilled in the art on a case-by-case basis by routine experimentation.

If desired, the bone particles can be modified in one or more ways, e.g., their protein content can be augmented or modified as described, for example, in U.S. Pat. Nos. 4,743,259 and 4,902,296, the contents of both of which are incorporated herein by reference.

Selection of Polymer

Practically any biocompatible polymer may be used in the composites of the invention. Co-polymers and/or polymer blends may also be exploited. The selected polymer preferably should be formable and settable under particular conditions. For example, the composite may become more formable when heated to or over a particular temperature, for example, a temperature at or above the glass transition temperature of the polymer component. Alternatively, the composite may be more formable when the polymer component has a certain cross-link density. After the composite is formed into the desired shape, the cross-link density of the polymer component of the composite is increased to render the composite less formable. In another embodiment, a small amount of monomer is mixed with the polymeric and bone components of the composite. Upon exposure to an energy source, e.g., UV light, the monomer and polymer will further polymerize, increasing the molecular weight, the cross-link density, or both.

If heat is employed to render the composite and/or the polymer component of the composite formable, the glass transition or melting temperature of the polymer component is preferably higher than normal body temperature, for example, higher than 40° C. Polymers that become more formable at higher temperatures, e.g., higher than 45°, 50°, or 55°, may also be used. Exemplary polymers having $T_g$ suitable for use with the invention include but are not limited to starch poly(caprolactone), poly(caprolactone), poly(l-lactide), poly(dl-lactide-co-glycolide), poly(l-lactide-co-dl-lactide), and co-polymers, mixtures, and enantiomers thereof.

It is not necessary for all embodiments that the glass transition temperature of the polymer be higher than body temperature. In non-load bearing and some load-bearing applications, the viscosity of the polymer need only be high enough that the composite will not flow out of the implant site. In other embodiments, the polymer component may have crystalline and non-crystalline regions. Depending on the ratio of crystalline and non-crystalline material, the polymer component may remain relatively rigid between the glass transition and melting temperatures. Indeed, for some polymers, the melting temperature will determine when the polymer component becomes formable.

Since the composite may be rendered formable just prior to implantation, polymer components with glass transition or melting temperatures higher than 60° C. are also suitable for use with the invention, despite the sensitivity of biological material to heat.

Potential damage to bone and/or other materials in the composite depends on both the temperature and the processing time. As the $T_g$ or $T_m$ of the polymer component increases, the composite should be heated for shorter periods of time to minimize damage to its biological components.

The $T_g$ of a polymer may be manipulated by adjusting its cross-link density and its molecular weight. Thus, for polymers whose glass transition temperatures are not sufficiently high, increasing the cross-link density or molecular weight can increase the $T_g$ to a level at which composites containing these polymers can be heated to render them formable.

Alternatively, the polymer may be produced with crystalline domains, increasing the stiffness of the polymer at temperatures above its glass transition temperature. In addition, the $T_g$ of the polymer component may be modified by adjusting the percentage of the crystalline component. Increasing the volume fraction of the crystalline domains may so reduce the formability of the polymer between $T_g$ and $T_m$ that the composite has to be heated above its melting point to be sufficiently formable for use with the invention.

Any biocompatible polymer may be used to form composites according to the invention. As noted above, the cross-link density and molecular weight of the polymer may need to be manipulated so that the polymer may be formed and set when desired. A number of biodegradable and non-biodegradable biocompatible polymers are known in the field of polymeric biomaterials, controlled drug release and tissue engineering (see, for example, U.S. Pat. Nos. 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, *Acc. Chem. Res.* 33:94, 2000; Langer, *J. Control Release* 62:7, 1999; and Uhrich et al., *Chem. Rev.* 99:3181, 1999, the contents of all of which are incorporated herein by reference).

Preferably, the polymer matrix is biodegradable. Exemplary biodegradable materials, in addition to those listed above, include but are not limited to poly(arylates), poly (anhydrides), poly(hydroxy acids), polyesters, poly(ortho esters), polycarbonates, poly(propylene fumerates), poly(amide esters), poly (amide carbonates), polyamides, polyamino acids, polyacetals, polylactides, polyglycolides, poly(dioxanones), polyhydroxybutyrate, polyhydroxyvalyrate, poly(vinyl pyrrolidone), biodegradable polycyanoacrylates, biodegradable polyurethanes, polyalkylene oxides, polymino carbonates, polyester amides, polyester imides, amino acid polyarylates, amino acid polycarbonates, and polysaccharides. Tyrosine-based polymers, including but not limited to polyarylates and polycarbonates, may also be employed (see Pulapura, et al., "Tyrosine-derived polycarbonates: Backbone-modified "pseudo"-poly(amino acids) designed for biomedical applications," *Biopolymers,* 1992, 32: 411-417; Hooper, et al., "Diphenolic monomers derived from the natural amino acid α-L-tyrosine: an evaluation of peptide coupling techniques," *J. Bioactive and Compatible Polymers,* 1995, 10:327-340, the contents of both of which are incorporated herein by reference).

Non-biodegradable polymers may also be used as well. For example, polypyrrole, polyanilines, polythiophene, and derivatives thereof are useful electroactive polymers that can transmit voltage from the endogenous bone to an implant. Other non-biodegradable, yet biocompatible polymers include polystyrene, non-biodegradable polyurethanes, polyureas, poly(ethylene vinyl acetate), polypropylene, polymethacrylate, polyethylene, and poly(ethylene oxide).

These polymers and the monomers that are used to produce any of these polymers are easily purchased from companies such as Polysciences, Sigma, and Scientific Polymer Products. Those skilled in the art will recognize that this is an exemplary, not a comprehensive, list of polymers appropriate for in vivo applications. Co-polymers, adducts, and/or blends of any of the polymers discussed herein may also be used in the practice of the invention.

In another embodiment, the composite is produced with a formable polymer and then hardened in situ. For example, the cross-link density of a polymer may be increased by exposing it to UV light or an alternative energy source. Alternatively, a photoactive cross-linking agent, chemical cross-linking agent, additional monomer, or combinations thereof may be mixed into the composite. Exposure to UV light after the composite is fitted to the implant site will increase one or both of the molecular weight and cross-link density, stiffening the polymer. The polymer component of the composite may also be softened by a solvent, e.g., ethanol. If a biocompatible solvent is used, the polymer may be hardened in situ or ex situ, for example, after molding. As the composite hardens, solvent leaving the composite material should be released into the surrounding tissue without causing undesirable effects such as irritation. If a non-biocompatible solvent is used, standard techniques such as vacuum, weight measurements, and chemical sampling may be used to determine whether sufficient amounts of the solvent has been removed from the composite before implantation in a patient.

Combining the Polymer and Bone

The polymer and the bone may be combined by any method known to those skilled in the art. For example, a homogenous mixture of polymer and bone particles may be pressed together at ambient or elevated temperatures. The pressed composite will maintain its shape and relative particle positioning. At elevated temperatures, the process may also be accomplished without pressure. Preferably, the polymer is not held at a temperature of greater than 80° C. for a significant time during mixing to prevent thermal damage to the biological component of the composite. Bone particles may be incorporated into a formable polymer by a variety of methods. For example, bone particles may also be mixed or folded into a polymer softened by heat or a solvent. Alternatively, a formable polymer may be formed into a sheet that is then covered with a layer of bone particles. The bone may then be forced into the polymer sheet using pressure. In another embodiment, bone particles are individually coated with polymer, for example, using a tumbler, spray coater, or a fluidized bed, before being mixed with a larger quantity of polymer. This facilitates even coating of the bone particles and improves integration of the bone particles and polymer.

Polymer processing techniques may also be used to combine the bone particles and polymer. For example, the polymer may be rendered formable, e.g., by heating or with a solvent, and combined with the bone particles by injection molding or extrusion forming. Alternatively, the polymer and bone particles may be mixed in a solvent and cast with or without pressure. The composite may be prepared from both formable and rigid polymers. For example, extrusion forming may be performed using pressure to manipulate a formable or rigid polymer. Once the composite is mixed, it may be desirable to store it in a container that imparts a static pressure to prevent separation of the bone particles and the polymer, which have different densities.

Alternatively, the polymer and bone may be supplied separately, e.g., in a kit, and mixed immediately prior to implantation or molding. The kit may contain a preset supply of bone-derived particles having certain sizes, shapes, and levels of demineralization. The surface of the bone-derived particles may have been modified using one or more of the techniques described herein. Alternatively, the kit may provide several different types of bone-derived particles of varying sizes, shapes, and levels of demineralization, and that may have been chemically modified in different ways. A surgeon or other professional may also combine the components in the kit with autologous tissue derived during surgery. For example, the surgeon may want to include autogenous tisue, e.g., bone marrow or bone shavings generated while preparing the implant site, into the composite.

These techniques may be used to prepare composites having a wide variety of configurations. For example, while most composites will employ a homogenous mixture of polymer and bone, it may be desirable to form a composite in which the bone is more highly concentrated on an exterior or an interior portion of the material. In addition, the composite need not be isotropic. Composites may be formed having different bone particle sizes, shapes, or volume fractions in different portions of the composite. For example, a composite may be formed having larger particles in an exterior portion and smaller particles in an interior portion, or vice versa. The composite may be formed with a gradient of particle types, sizes, size distributions, shapes, densities, or volume fractions. The distribution of particles may be centrosymmetric, may reflect some other symmetry, or may be asymmetric. If the composite is formed in sections, e.g., having different arrangements, densities, volume fractions, etc. of particles, various polymer joining techniques, for example, adhesives or mechanical fasteners, may be used to unite the sections into a single implant. For example, ultrasonic welding will enable the polymer at the boundaries between the sections to blend with the particles without significantly disturbing the arrangement of the particles.

Elongated particles may be distributed in the polymer in a variety of arrangements. For example, elongated particles may be aligned in a particular direction throughout the composite. Alternatively, the composite may be assembled in layers and the orientation of the elongate particles rotated by some angle, e.g. 90° or 45°, in each layer. Smaller angles may be used to form a helical pattern. Alternatively or in addition, elongated bone particles may be used in one portion of the composite while more regularly dimensioned particles are used in another.

To align elongated particles, the composite may be rolled, extruded, twisted, or otherwise mechanically aligned. Alternatively, the elongated particles may be deposited into the polymer as they are produced. For example, grated or milled bone particles tend to exit the milling apparatus roughly aligned with one another. Instead of being collected, the particles may be delivered directly from the mill to the softened polymer, onto which they will fall in roughly the same orientation, much like cheese passing through a plane grater. A static electric charge imparted to the bone particles can also facilitate alignment. Friction generated during milling (if the apparatus is not water-coated) or sieving may be sufficient to cause alignment. Alternatively, an electric field may be created across a sieve to impart added charge. Producing randomly oriented particles requires other techniques. Mechanical stirring usually produces areas of local alignment. Bubbling may impart a slight upwards orientation but otherwise can effectively randomize the orientation of the particles. Agitation may also be an effective process to randomize orientation.

The composite may include practically any ratio of polymer and bone, for example, between about 5 weight % polymer and about 90 weight % polymer. For example, the composite may include about 25% to about 30% polymer or approximately equal weights of polymer and bone. The proportions of the polymer and bone can influence various characteristics of the composite, for example, its mechanical properties, including fatigue, and the degradation rate. In addition, the cellular response to the composite will vary with the proportion of polymer and bone. One skilled in the art will recognize that standard experimental techniques may be used to test these properties for a range of compositions to optimize a composite for a desired application. For example, standard mechanical testing instruments may be used to test the compressive strength and stiffness of the composite.

Cells may be cultured on the composite for an appropriate period of time and the metabolic products and the amount of proliferation (e.g., the number of cells in comparison to the number of cells seeded) analyzed. The weight change of the composite may be measured after incubation in saline or other fluids. Repeated analysis will demonstrate whether degradation is linear or not, and mechanical testing of the incubated material will show the change in mechanical properties as the composite degrades. Such testing may also be used to compare the enzymatic and non-enzymatic degradation of the composite and to determine the levels of enzymatic degradation.

Mechanical Considerations

In a preferred embodiment, the bone particles in the composite, rather than the polymer matrix, carry the majority of the applied load, while the polymer matrix holds the particles in place. For example, larger pieces of bone may be stacked on top of one another in a pre-form and polymer allowed to flow around the bone pieces, following which the polymer is allowed to set. The polymer component of the composite may be rendered formable to implant the composite into a tissue site. For example, a surgeon can manipulate a composite within a formable component to fit a specific patient site during surgery. This allows structural implants of a desired shape to be produced from irregularly shaped pieces of bone. Cortical bone has relatively high compressive strength; however, the forces exerted at the polymer-filled boundaries between bone pieces will have a shear component.

In an alternative embodiment, the surfaces of the bone particles are demineralized, following which the exposed collagen of adjacent bone particles is cross-linked using the techniques of our commonly owned U.S. Pat. No. 6,123,731, entitled Osteoimplant and Method for its Manufacture, the contents of which are incorporated herein by reference. Exemplary cross-linking methods include chemical reaction, irradiation, application of heat, dehydrothermal treatment, enzymatic treatment, etc. Alternatively or in addition, where bone particles having varying degrees of demineralization are used, bone particles may be bonded to one another by linking exposed collagen of demineralized particles to the inorganic component of non-demineralized bone particles using coupling agents, for example, silane coupling agents. In a further embodiment, the mineral content of the particle surfaces may be enhanced by rinsing with phosphoric acid, e.g., 1 to 15 minutes in a 5-50% solution by volume. Alternatively, bone particles may be treated to induce deposition of one or more of hydroxyapatite, tricalcium phosphate, polycrystalline calcium, calcium carbonate, coralline calcium, calcium phosphate, calcium hydrogen phosphate, calcium phosphosilicate, tetrabasic calcium phosphate, sodium chondroitin sulfate, sodium succinate anhydride, calcium sulfate, magnesium stearate, calcium sulfate dihydrate, polyvinyl pyrrolidone, propylene glycol-co-fumaric acid, calcified polyurethane, baria-boroalumino-silicate glass, and/or polylactide-co-glycolide deposition and crystal formation on exposed collagen fibers. The polymer will form around these fibers, increasing interfacial area and improving the wet strength of the composite.

Additional Components

Additional materials may be included in the composite. Autologous tissues such as bone marrow and bone particles may be combined with the already mixed composite or mixed with polymer and bone particles from a kit to form the composite immediately before implantation. The composite may include additional calcium-based ceramics such as calcium phosphate and calcium carbonate. Non-biologically active materials may also be incorporated into the composite. For example, radiopaque, luminescent, or magnetically active particles may be attached to the bone particles using silane chemistry or other coupling agents, for example zirconates and titanates, or mixed into the polymer as part of the composite. Alternatively, or in addition, poly(ethylene glycol) (PEG) may be attached to the bone particles. Biologically active molecules, for example, small molecules, bioactive agents, and biomolecules such as lipids may be linked to the bone particles through silane SAMs, using a polysialic acid linker (see, for example, U.S. Pat. No. 5,846,951) or with m-maleimidobenzoyl-N-hydroxysuccinimide ester, beta-maleimidopropionic acid N-hydroxysuccinimide ester, or succinic anhydride. Equistar of Houston Tex. manufactures INTEGRATE™ resins, polyolefins that have been chemically modified to provide polar anhydride functionality on the polymer backbone. The polar functionality allows these products to function as coupling agents in blends of dissimilar materials, promote compatibility in polymer blends and to provide improved bonding in adhesive formulations. Coupling agents may be used between bone and the polymer component in order to enhance bonding at the bone/polymer interfaces of the composite. For example, silane groups may be incorporated into the polymer as a side chain or by modifying the polymer after polymerization. The silane groups may then be attached to bone particles. Alternatively, coupling agents having reactive end groups may be attached to the bone particles and then reacted with the polymer.

Biologically active materials, including biomolecules, small molecules, and bioactive agents may also be combined with the polymer and bone to, for example, stimulate particular metabolic functions, recruit cells, or reduce inflammation. For example, nucleic acid vectors, including plasmids and viral vectors, that will be introduced into the patient's cells and cause the production of growth factors such as bone morphogenetic proteins may be included in the composite. RNAi, anti-sense RNA or other technologies may be used to reduce the production of various factors. These materials need not be covalently bonded to either component of the composite. A material may be selectively distributed on or near the surface of the composite using the layering techniques described above. While the surface of the composite will be mixed somewhat as the composite is manipulated in the implant site, the thickness of the surface layer will ensure that at least a portion of the surface layer of the composite remains at the surface of the implant. Alternatively or in addition, biologically active components may be covalently linked to the bone particles before combination with the polymer. For example, silane coupling agents having amine, carboxyl, hydroxyl, or mercapto groups may be attached to the bone particles through the silane and then to reactive groups on a biomolecule, small molecule, or bioactive agent.

The composite may also be seeded with cells. For example, a patient's own cells may be harvested, expanded, and mixed with the composite. Alternatively, stem cells or exogenous cells may be employed. Exemplary cells for use with the invention include mesenchymal stem cells and connective tissue cells, including osteoblasts, osteoclasts, and fibroblasts.

The collagen fibers exposed by demineralization are typically relatively chemically inert. The collagen may be rendered more reactive by fraying the triple helical structure of the collagen to partially or fully separate the individual collagen strands from each other. Rinsing the partially demineralized bone particles in an alkaline solution will fray the collagen fibrils. For example, bone particles may be mixed with water at a pH of about 10 for about 8 hours, after which the solution is neutralized. One skilled in the art will recognize that the pH, the time period, or both may be adjusted to modify the extent of fraying. Agitation, for example, in an ultrasonic bath, may reduce the processing time. Alternatively, the particles may be sonicated with water, surfactant, alcohol, or some combination of these. Both frayed and unfrayed collagen fibers may be derivatized with biomolecules, small molecules, bioactive molecules, biologically inactive compounds, or some combination of these. These materials may be covalently or non-covalently linked to the exposed collagen strands through reactive amino acids on the collagen fiber such as lysine, arginine, hydroxylysine, proline, and hydroxyproline.

Implantation of the Composite

The composite may be implanted directly into a tissue site or formed into a shape immediately prior to and/or for a period after implantation. Alternatively, or in addition, the shape of the composite may be manipulated before, during, or for a period after implantation. The term "immediately prior" is used to indicate that the desired shape is identified, the composite formed into the shape, and the shaped composite implanted into a patient as part of a surgical procedure.

Because the composite can be formed and manipulated in situ, a surgeon does not need to know the exact size or shape of the implant site before scheduling a procedure to fill it. In addition, the surgeon does not need to schedule an additional procedure or prolong surgery to prepare the implant site before implantation. Rather, once the characteristics of the implant site are known, the composite is shaped to match it.

In one embodiment, a series of molds of a particular bone or bone portion are available to a surgeon during surgery. After determining the dimensions of the implant site, the surgeon forms the composite in the appropriate mold, allows the composite to harden, and implants the newly formed implant into the patient. As noted above, the composite may be produced with the polymer in a softened state or softened by the user immediately before forming. The user may then initiate setting of the composite after it is formed. In one embodiment, a surgeon opens a package of formable composite and shapes it during surgery to the exact shape of the patient site.

In an alternative embodiment, the softened composite is formed in the implant site. For example, a bony defect may be filled by the formable composite. The composite is pressed into the defect site to ensure that it fills all the small spaces of the site. If the composite is softened by the user for forming in the implant site, it is preferably softened by heat or other energy, although a biocompatible solvent may be used as well. In one embodiment, the polymer undergoes a conformational change upon application of a particular wavelength of light to become formable. The polymer may simply relax over time to set or may set upon exposure to a different wavelength of light.

In embodiments where the polymer component becomes formable when heated, the heat absorbed by bone particles in the composite may increase the cooling time of the composite, extending the time available to form the composite into an implant. Depending on the relative heat capacities of the bone and the polymer components and the size of the bone particles, the bone may continue to release heat into the surrounding polymer after the time when the polymer alone would have cooled. The size and density distribution of bone particles within the composite may be optimized to adjust the amount of heat released into portions of an osteoimplant during and after implantation.

The composite may be formed, machined, or both, into a variety of shapes. Exemplary shapes include, without limitation, sheet, plate, particle, sphere, hemisphere strand, coiled strand, capillary network, film, fiber, mesh, disk, cone, portion of a cone, pin, screw, tube, cup, tooth, tooth root, strut, wedge, portion of wedge, cylinder, threaded cylinder, rod, hinge, rivet, anchor, spheroid, ellipsoid, oblate spheroid, prolate ellipsoid, or hyperbolic paraboloid. In one embodiment, the composite is formed in a mold having the shape of a desired implant. For example, a mold may be shaped as a portion of a bone or as a whole bone that is being replaced. Exemplary bones that may be replaced using the techniques of the invention include ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, incus, malleus, stapes, ilium, ischium, pubis, femur, tibia, fibula, patella, calcaneus, tarsal and metatarsal bones. In another embodiment, the composite is formed as a plate or similar support, including but not limited to an I-shape to be placed between teeth for intra-bony defects, a crescent apron for single site use, a rectangular bib for defects including both the buccal and lingual alveolar ridges, neutralization plates, spoon plates, condylar plates, clover leaf plates, compression plates, bridge plates, wave plates, etc. Partial tubular as well as flat plates may be fabricated using the composite of the invention. Alternatively, the composite may be a block that is machined into a desired shape. The composite may be machined in either its set condition or its formable condition. Such machining might be simpler for an end user, such as a surgeon, when the composite is in its formable condition.

If desired, mechanical fasteners such as screws, rivets, or sutures may be used to improve the retention of the implant. In one embodiment, no drilling is required to fix the fastener to the implant. Rather, the fastener is inserted into the composite while it is still pliable or while the polymer and the bone particles are being mixed. Of course, the rigid composite may be drilled if desired. If the shape of the final implant is somehow incorrect, composites that are softened by heating may be reheated and the shape readjusted.

EXAMPLES

Polymer pellets of starch poly(caprolactone) were placed in a microwave oven and heated to approximately 130° F. (54.4° C.). The pellets were then pressed together by hand to form a larger mass of polymer. Before the polymer cooled, partially demineralized bovine bone particles were folded into the polymer until the polymer contained approximately 50% by weight of bone particles. The composite was then heated and formed into the desired final shape. Upon cooling to normal body temperature, the composite set to form a rigid construct in the desired shape. The composite could be repeatedly heated and reshaped. Once formed, the composite was subjected to approximately 10 heating/cooling cycles with no observable degradation of handling or setting properties.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A composite osteoimplant, comprising:
a polymer, wherein the polymer is selected from the group consisting of starch poly(caprolactone), poly(caprolactone), poly(l-lactide), poly(dl-lactide-co-glycolide), poly(l-lactide-co-dl-lactide), enantiomers of the above, co-polymers of the above, and mixtures of the above; and
bone-derived particles; wherein the composite is formable during implantation or immediately prior to implantation and is settable under suitable conditions; and wherein the composite is not formable at about 37° C., and wherein the composite becomes formable when heated to a temperature greater than about 40° C.

2. The osteoimplant of claim 1, wherein the composite becomes formable when heated to a temperature greater than about 45° C.

3. The osteoimplant of claim 2, wherein the composite becomes formable when heated to a temperature greater than about 50° C.

4. The osteoimplant of claim 3, wherein the composite becomes formable when heated to a temperature greater than about 55° C.

5. The osteoimplant of claim 4, wherein the composite becomes formable when heated to a temperature greater than about 60° C.

6. The osteoimplant of claim 5, wherein the composite becomes formable when heated to a temperature greater than about 70° C.

7. The osteoimplant of claim 6, wherein the composite becomes formable when heated to a temperature greater than about 80° C.

8. The osteoimplant of claim 7, wherein the composite becomes formable when heated to a temperature greater than about 90° C.

9. The osteoimplant of claim 1, wherein the composite is set by increasing the cross-link density of the polymer component.

10. The osteoimplant of claim 1, wherein the composite further comprises a monomer, the composite becoming set when the monomer is covalently incorporated into the polymer.

11. The osteoimplant of claim 1, wherein the composite further comprises at least one member selected from the group consisting of bone marrow, biomolecules, small molecules, bioactive agents, calcium phosphate, calcium carbonate, and cells.

12. The osteoimplant of claim 1, wherein the composite further comprises at least one member of nucleic acid vectors, mesenchymal stem cells, osteoblasts, osteoclasts, and fibroblasts.

13. The osteoimplant of claim 12, wherein the nucleic acid vector, when introduced into a cell, increases the cell's production of bone morphogenetic proteins.

14. The osteoimplant of claim 1, wherein the osteoimplant is capable of being irrigated following implantation without substantially changing its shape.

15. The osteoimplant of claim 1, wherein the bone-derived particles are selected from the group consisting of nondemineralized bone particles, partially demineralized bone particles, superficially demineralized bone particles, fully demineralized bone particles and mixtures thereof.

16. The osteoimplant of claim 1, wherein the bone-derived particles are obtained from a member of the group consisting of cortical bone, cancellous bone, cortico-cancellous bone, and mixtures thereof.

17. The osteoimplant of claim 1, wherein the bone-derived particles are obtained from a member of the group consisting of autogenous bone, allogenic bone, xenogeneic bone, transgenic bone, and mixtures thereof.

18. The osteoimplant of claim 1, wherein the bone-derived particles are about 10% to about 99% by weight of the composite.

19. The osteoimplant of claim 18, wherein the bone-derived particles are about 25% to about 50% by weight of the composite.

20. The osteoimplant of claim 1, wherein a surface of the bone-derived particles is modified with at least one member selected from the group consisting of biomolecules, small molecules, bioactive agents, non-biologically active materials, and any combination of the above.

21. The osteoimplant of claim 20, wherein the member is linked to the surface by a coupling agent.

22. The osteoimplant of claim 1, wherein at least a portion of the bone-derived particles are covalently linked to one another.

23. The osteoimplant of claim 1, wherein collagen fibers at the surface of the bone-derived particles are exposed.

24. The osteoimplant of claim 23, wherein the exposed collagen fibers are partially or fully separated from one another.

25. The osteoimplant of claim 23, wherein the exposed collagen fibers are derivatized with a moiety selected from the group consisting of biomolecules, small molecules, bioactive agents, non-biologically active materials, and any combination of the above.

26. The osteoimplant of claim 1, wherein the polymer comprises poly(caprolactone).

27. The osteoimplant of claim 1, wherein the bone derived particles and the polymer are linked with a coupling agent.

28. The osteoimplant of claim 1, wherein the osteoimplant has a shape selected from the group consisting of bone, a section of a bone, sheet, plate, particle, sphere, hemisphere strand, coiled strand, capillary network, film, fiber, mesh, disk, cone, portion of a cone, pin, screw, tube, cup, tooth, tooth root, strut, wedge, portion of wedge, cylinder, threaded cylinder, rod, hinge, rivet, anchor, spheroid, ellipsoid, oblate spheroid, prolate ellipsoid, and hyperbolic paraboloid.

29. The osteoimplant of claim 1, wherein the osteoimplant comprises a plurality of pieces of composite, wherein the pieces are joined together.

30. The osteoimplant of claim 29, wherein the pieces are joined together with a member selected from the group consisting of adhesives, mechanical fasteners, ultrasonic bonding, and any combination of the above.

31. The osteoimplant of claim 1, wherein the composite is adapted and constructed to be formed in a mold.

32. The osteoimplant of claim 1, wherein the distribution of bone-derived particles within the composite is not uniform with respect to a member of the group consisting of volume fraction, size, density, shape, size distribution, and any combination of the above.

33. The osteoimplant of claim 1, wherein at least a portion of the bone-derived particles in the composite are elongate, and wherein an arrangement of bone-derived particles in the composite is isotropic or anisotropic.

34. The osteoimplant of claim 1, wherein at least a portion of the bone-derived particles in the composite are elongate, and wherein a relative alignment of bone-derived particles in a first portion of the composite is different than the relative alignment of bone-derived particles in a second portion of the composite.

* * * * *